United States Patent
Georgeson et al.

(10) Patent No.: US 6,748,791 B1
(45) Date of Patent: *Jun. 15, 2004

(54) DAMAGE DETECTION DEVICE AND METHOD

(75) Inventors: Gary E. Georgeson, Federal Way, WA (US); Jeffrey M. Hansen, Renton, WA (US); Jeffrey R. Kollgaard, Kent, WA (US); Scott W. Lea, Renton, WA (US); J. Robert Bopp, Kent, WA (US)

(73) Assignee: The Boeing Company, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 893 days.

(21) Appl. No.: 08/944,885

(22) Filed: Oct. 6, 1997

Related U.S. Application Data

(60) Provisional application No. 60/028,509, filed on Oct. 18, 1996.

(51) Int. Cl.$^7$ ................................................ G01M 7/00
(52) U.S. Cl. ...................... 73/12.13; 73/12.01; 73/12.06
(58) Field of Search ........................... 73/12.01, 12.04, 73/12.05, 12.06, 12.07, 12.13

(56) References Cited

U.S. PATENT DOCUMENTS

| | | | |
|---|---|---|---|
| 2,531,782 A | 11/1950 | Moore | |
| 3,187,242 A | 6/1965 | Schick | |
| 3,239,913 A | 3/1966 | Richmond | |
| 4,489,123 A | 12/1984 | Schijve et al. | |
| 4,808,461 A | 2/1989 | Boyce et al. | |
| 4,875,616 A | 10/1989 | Nixdorf | |
| 5,003,811 A | * 4/1991 | Shannon et al. | 73/12.14 |
| 5,041,321 A | 8/1991 | Bendig | |
| 5,048,320 A | * 9/1991 | Mitsuhashi et al. | 73/12.09 |
| 5,115,962 A | 5/1992 | Anderson et al. | |
| 5,186,776 A | 2/1993 | Boyce et al. | |
| 5,376,598 A | 12/1994 | Preedy et al. | |
| 5,441,682 A | 8/1995 | Baker | |
| 5,445,861 A | 8/1995 | Newton et al. | |
| 5,466,506 A | 11/1995 | Freitas et al. | |
| 5,490,411 A | * 2/1996 | Hogan | 73/12.13 |
| 5,589,635 A | 12/1996 | Baudrillard et al. | |
| 5,696,312 A | * 12/1997 | Lee et al. | 73/12.13 |
| 5,739,411 A | * 4/1998 | Lee et al. | 73/12.09 |

FOREIGN PATENT DOCUMENTS

JP      205116      12/1982

* cited by examiner

*Primary Examiner*—Max Noori
(74) *Attorney, Agent, or Firm*—John C. Hammar

(57) ABSTRACT

A damage detection device is used to detect damage in bonded and laminated composite structures. A tap hammer or tap coin containing an acceleration sensor is connected to a circuit that can measure the width of an impact signal and then display the result. The result correlates to local stiffness of a structure. A method of determining the desired signal width and the method of using the damage detection device, includes tapping a known good region and then tapping a suspect region. Readings from the two areas are used to determine whether the suspect region is within an acceptable range. The circuit determines the desired signal width by measuring from the time the impact signal exceeds a threshold to the time it falls below the threshold.

5 Claims, 7 Drawing Sheets

DAMAGE DETECTION DEVICE AND METHOD

REFERENCE TO RELATED APPLICATION

The present application claims the benefit of U.S. Provisional Application No. 60/028,509, filed Oct. 18, 1996.

TECHNICAL FIELD

The present invention relates to an apparatus and method for rapidly locating and determining the extent of damage in bonded and solid laminate structures, particularly fiber-reinforced resin matrix composites.

BACKGROUND OF THE INVENTION

Bonded metal and composite structures and monolithic metal and composite structures are widely used in the manufacture of aircraft. The percentage of composite materials being used on aircraft automobiles, boats, and in building construction materials continues to rise. Use increases the need for Non-Destructive Inspection (NDI) methods that can effectively identify composite degradation and damage. Delamination caused by impact can significantly reduce the strength or stiffness of a composite without being visible to the naked eye. A simple, cost effective inspection method to detect such defects is needed. Methods such as echo ultrasonics, shearography, and thermography are costly to implement. These methods also often require highly trained operators to implement, and specialized, bulky equipment.

A simple composite NDI technique is the coin-tap or tap hammer method. In this method, the inspector will use an ordinary coin, such as a U.S. quarter, or a small hammer to tap along the structure and listen for a change in the sound. This method works because of the difference in the sound produced by a bad (e.g., delaminated) region versus a good region. A good region tends to ring while a bad region will sound dead. The mechanics of the tap testing method have been studied in detail by P. Cawley and R. D. Adams, who published, for example: Sound & Vibration, 122,(2), 299 (1988); Mat'l Eval., 47, 558 (1989), Brit. J. NDT, [32(9) 454 (1990); Int'l Conf. Structural Adhesives in Eng'g, C19, 139 (1986), or U.S. Pat. No. 5,589,635, which we incorporate by reference. Theoretical and experimental results from the Cawley and Adams work demonstrate the viability of using changes in features of the force-time curve of the impact as an indication of the local integrity of the structure. Damage, such as a disbond, results in a local decrease in the stiffness of the structure, which changes the force-time curve that a tap near the damage produces. The difference in the audible sound tells one that the force-time curves differ, but the tap method is difficult to implement in a noisy environment. The amplitude, duration, and frequency response of the impact curve are all affected by the local stiffness, and under various conditions can be flagged as indicators of defects and damage.

Although it is cheap and simple, the tap method has several drawbacks. It depends upon the inspector's hearing, experience, and interpretation. The results are subject to interference from workplace noise. Workplace noise is especially a problem in an on-aircraft, flightline environment. The traditional tap method is unable to provide quantitative data. Quantitative data would provide a clearer indication for the flightline inspector to make a fly or no-fly determination. Tapping on the surface with a coin or tap hammer and listening to the tone of the part is adequate for limited detection. It is subjective and is often imprecise. Approaches to overcome these drawbacks continue to be relatively expensive and are of limited practical use for on-aircraft inspection.

SUMMARY OF THE INVENTION

The damage detection device makes it easy to locate damage to both solid and bonded surfaces, such as an aircraft wing skin, a car door, a boat hull, or the like. The device does not change the operator's ability to listen for audible tonal changes, but it provides a quantitative reference number in microseconds that represents the state of stiffness of the surface. This time measurement can be correlated to a level of damage. The ability to locate damage using an instrument that provides a reference number will increase the confidence of the technician and both the accuracy and repeatability of the inspection.

We have developed a simple low cost instrumented tap hammer that provides a quantitative measure of the hammer/composite impulse time. We have correlated the time (duration) measured with the amount of damage (delaminations) in the structure. The instrumented tap hammer of the present invention supplements the tonal discrimination of the operator with a numeric readout that can readily be related to local part quality. The effect of background noise and operator differences on the inspection results can be eliminated. An increased sensitivity is also shown over the audible tap test method.

In a preferred embodiment our damage detection device includes a tap hammer with an acceleration sensor mounted in the head of the hammer. A wire connects the sensor to an analysis circuit that converts an impact signal from the hammer into a readout value. The circuit measures a time in microseconds during which the impact signal remains above a predetermined threshold. The readout value is then shown on a display.

A second, miniaturized embodiment of the device includes an acceleration sensor, a circuit, and a display, in the shape of or mounted on a slug or a coin. The inspector taps the structure with the acceleration sensor like the coin tap method to produce an impact signal which the circuit converts to a readout value, which is displayed. The readout can be "pass/fail," the impulse time, or some other information, as desired.

The damage detection device, including a tap hammer, is inexpensive and easy to use. It provides quantitative results without relying on elaborate or expensive circuitry. The slug or coin device, is small, easy to use, and extremely portable. It is used just like the current coin tapping process, but with more positive results. The readout provides a quantitative value to assess the condition, even if there is significant background noise.

The damage detection device addresses the genuine need for a low cost instrumented non-destructive evaluation (NDE) method for factory or field testing of composite commercial and military aircraft. The results of testing demonstrate the benefit of a quantitative indication of the local stiffness (as measured by the impact pulse width). The use of the damage detection device provides a clear improvement over the traditional coin tap method by reducing its subjectivity, increasing its sensitivity, and quantifying the actual impact response.

The skin thickness is an important consideration in whether a composite can be effectively inspected. As the skin thickness increases, the difference between the response of "good" and disbonded skin will get smaller. The effective range for the damage detection device was 1–7 plies on fiberglass/epoxy facesheets of the sandwich panels tested. The range will depend upon the material and type of structure, as well as the defect type, size, and depth. We are able to detect delaminations in 6 mm thick graphite/epoxy composite laminates.

DETAILED DESCRIPTION OF A PREFERRED EMBODIMENT

Figure 1:
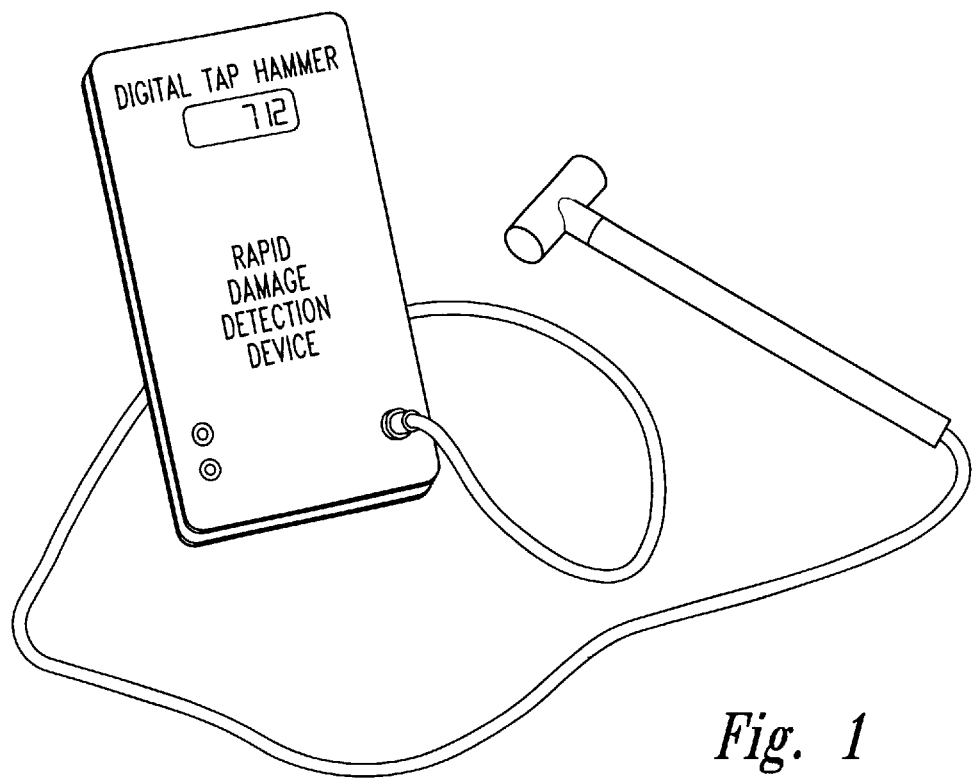
FIG. 1 is a schematic of a preferred damage detection device of the present invention.

The damage detection device of the present invention consists of a tap hammer containing an accelerometer electrically connected by cable through the handle to a hand-held module containing digital logic components and a liquid crystal digital display. A photograph of the rapid damage detection device is shown in FIG. 1. The user interface features of the damage detection device include:

Hand held, low cost inspection system;
Low weight detection hammer;
Large 0.35 inch display of digital values;
Automatic display reset;
Scope monitor jack for hammer signal evaluation;
Hours of continuous operation;
Powered by high output rechargeable Nickel-Cadmium batteries;
Battery recharge jack;
Low battery light-emitting drode (LED); and
Durable impact resistant case.

For purposes of this description, "laminate" means a fiber-reinforced organic resin matrix composite having a plurality of plies of prepreg or its equivalent consolidated together and cured, as appropriate. The laminates are prefabricated by any appropriate means including automatic or hand tape lay up or tow fiber placement with autoclave consolidation and cure; resin transfer molding (RTM); SCRIMP (e.g., U.S. Pat. Nos. 4,902,215 or 5,316,462); or the like. Generally, the organic matrix resin is a thermoplastic, especially PEK, PEEK, PEKK, ULTEM polyimide, or KIII. In the welding operation, resin in the laminates as well as resin in the susceptor melts, intermixes, and fuses to form the weld. The laminate might also be a thermoset in which case the welding process actually forms a hot melt adhesive bond rather than a weld. We prefer welding, but recognize the analogous process of adhesive bonding of thermosets.

In a thermoplastic laminate, the reinforcing fiber typically is carbon fiber in continuous or chopped form, and generally as tow or woven fabric. While other fibers can be used, modern aerospace requirements most often dictate carbon fibers for their strength and durability, and we prefer them. In thermosets, especially epoxy, the fibers might be graphite or fiberglass.

Figure 2:
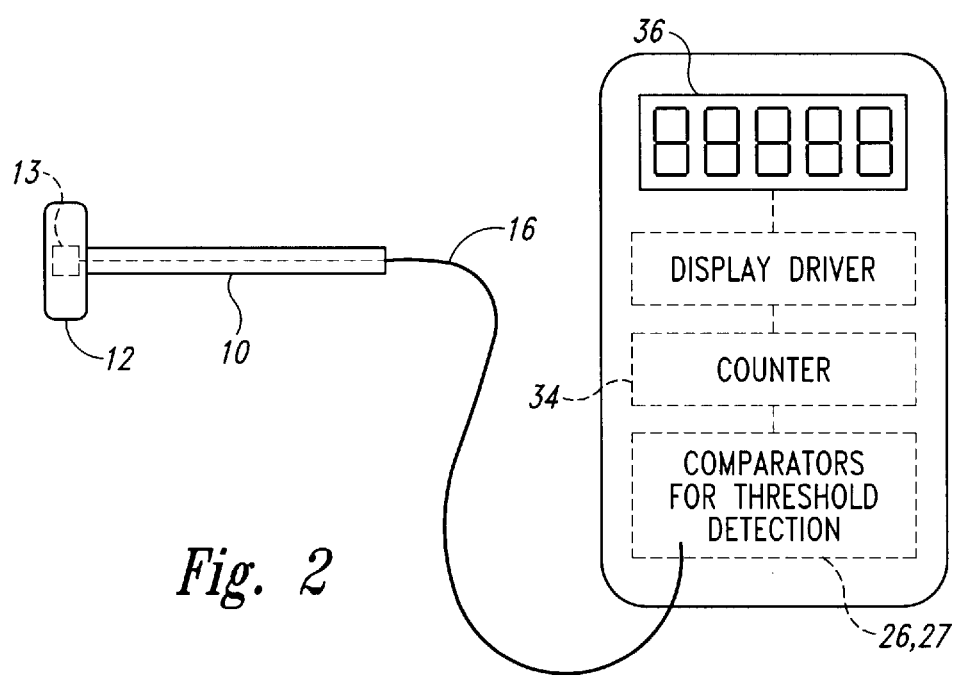
FIG. 2 is a diagramatic view of a typical damage detection device.

Referring to FIG. 2, a damage detection device includes a hammer 10 with a head 12 and a handle 14. A cable 16 runs through the handle and connects the hammer head 12 to a box that contains a readout display 18. A high gain accelerometer 13 is mounted inside the hammer head 12 and is connected to the cable 16. The device circuitry converts the impact signal into a readout.

We examined the impact pulse shape in some preliminary experiments using a tap hammer with an accelerometer mounted on the head. The accelerometer was connected to an oscilloscope, which displayed its response to each tap. A surprising result was that the impact width is relatively insensitive to the magnitude of the hammer hit, but very sensitive to the local stiffness of the laminate. This finding can eliminate the need for a controlled "tapper," such as the one described in Adams and Cawley, *Int. Conf on Structural Adhesives in Eng.* C19, 139 (1986). Adam and Cawley suggest that a constant pulse amplitude is necessary to obtain "good" data. Impact pulse duration can correlate with flaw extent in both laminates and sandwich structures, even over the range of tap amplitudes common to a traditional tap test. Human control of the magnitude of the taps is generally sufficient, so the hand-held tap hammer does not have to be abandoned for a more precise (and considerably more expensive) electro-mechanical "tapper." Actual data illustrates the precision of the hand-held approach.

Figure 3:
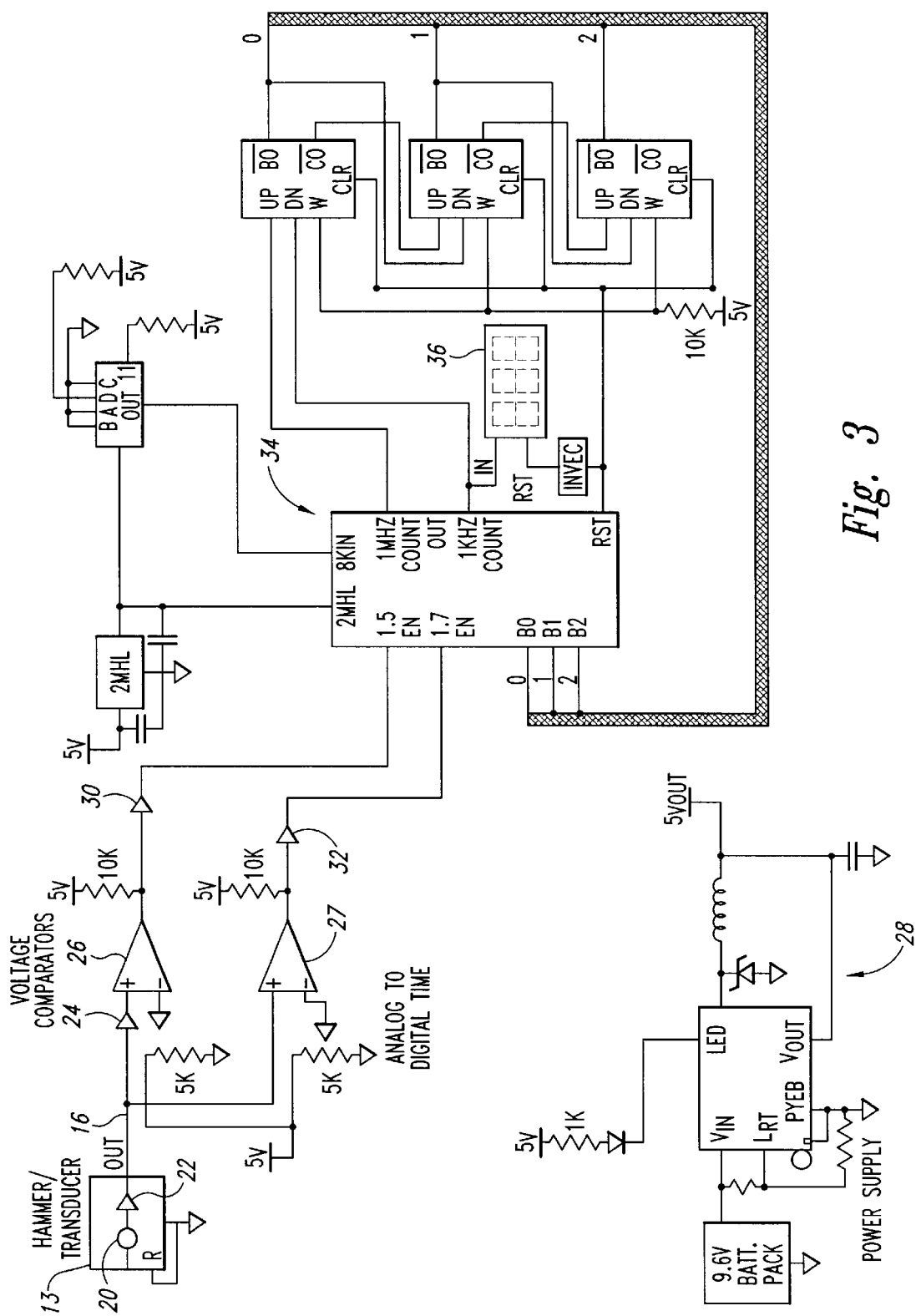
FIG. 3 is a circuit diagram of the circuitry used in a preferred embodiment of the present invention.

FIG. 3 shows the converting circuit for analyzing the impact signal. The acceleration sensor receives an impact signal 20 when the hammer head is struck against a structure that is being inspected. The impact signal 20 is fed into an amplifier circuit 22 that multiplies the voltage output and sends an amplified impact signal 24 to a pair of comparator amplifiers 26 and 27. The gain on the acceleration signal is set to a high gain such that the output signal is clipped at the supply voltage 28 (i.e., 5 Volts). The first comparator 26 acts as a threshold detector and produces a high output signal 30 when the impact signal exceeds a triggering threshold value. The triggering threshold value was set at 1.5 Volts in our tests, although this level will depend on the type of signal received and may vary from application to application. This high signal 30 lasts as long as the impact signal 20 is higher than the lower threshold voltage. The second comparator 27 also acts as a threshold detector to produce a high output signal 32 when the impact signal reaches or exceeds a high threshold voltage. The high threshold voltage was set at 4.5 V, although this voltage level may be set at any appropriate level depending on the application. The high threshold indicates that the tap had adequate energy.

The signals from the first comparator 26 and the second comparator 27 are fed into a logic device 34. The logic device 34 determines how long the signal from the first comparator 26 remains high (i.e., above the triggering threshold) and whether the second comparator 27 ever produced a high output signal. The logic device 34 will drive a display 36 to display a time for the duration of the impact signal above the triggering threshold, if the high threshold has been reached. If the high threshold has not been reached, the logic device will determine that no measurable reading was obtained. There are many ways known to those skilled in the art for converting and displaying the duration of the high signal from the first comparator, such as inputting the signal from the first comparator into an AND gate along with a signal from a digital clock. This signal may then be introduced to a counter that can then drive a display that will show the count. If the clock were set to produce a 1 MHz pulse rate, the counts would correspond to a time duration measured in microseconds. In this manner a signal is displayed which corresponds to the duration that the impact signal exceeds a lower threshold level as measured in microseconds.

Figure 7A:
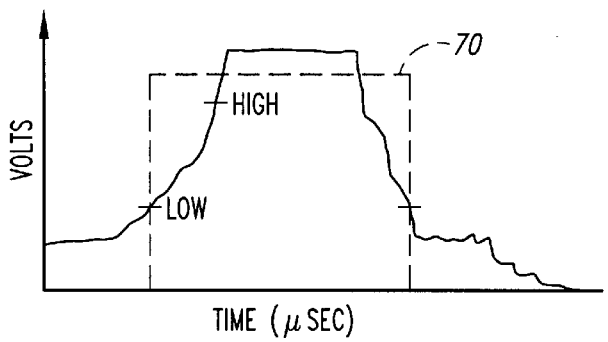
FIG. 7A is a representation of the oscilloscope signal showing an impact signal waveform for a bad region with the first comparator output superimposed.
Figure 7B:
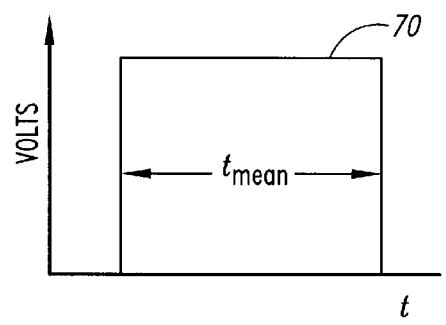
FIG. 7B represents the output from the first comparator for a bad region.

The width of the force-time pulse correlates to the mechanical impedance of the local structure being tapped. A delamination in a composite skin or a disbond between the skin and the core of a sandwich panel will tend to reduce the local stiffness and will produce a wider force-time pulse (FIGS. 7A and 7B). Potting in the core of a sandwich panel will increase the local stiffness, and produce a narrower pulse than nominal. Therefore, deviation from nominal width indicates a deviation from nominal structure. The amplitude of the pulse does not affect the width as one would expect. A precisely controlled impact is not required if the gates are chosen carefully. Within a broad range of impact levels, the impact width measured at a particular location is relatively constant. Different operators tapping at various levels produce similar impact widths with similar spreads. Ply drops will reduce the local stiffness, and will increase the average pulse width and number displayed. Therefore, knowledge of the design of the skin is essential to identifying true flaws.

The damage detection device having an accelerometer, a power source (such as a battery), an analysis circuit, and a display 56 can be miniaturized to a size suitable for mounting on a slug or coin. This miniaturized device would allow inspectors to do a traditional coin-tap method inspection, while providing additional quantitative data. The reduced size allows the inspector to carry the device while working on a flightline. Since the device is in the form of a coin similar to that used in a traditional coin tap method, little training would be required in the use of the damage measurement device.

Figure 4:
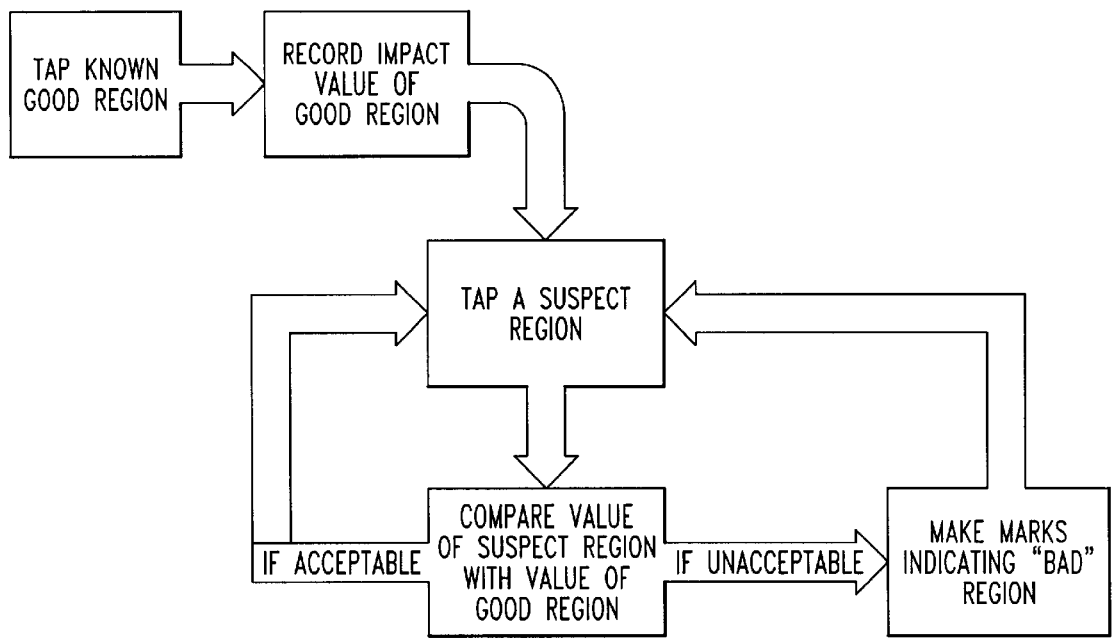
FIG. 4 is a flow chart of the tap method used in the damage detection device.

FIG. 4 shows a diagram of the method by which a region would be inspected using our damage detection method. The inspector would first tap a known good region and obtain a value. The value would be recorded or remembered. The operator would then tap a suspect region and compare the displayed reading with the reading obtained from the good region. If the suspect region were acceptable, i.e., the tap was within the tolerance of a good region, the inspector would tap again at another suspect region. If the suspect region were unacceptable, the region could be marked and then another suspect region could be tapped. This procedure would continue until the inspector had mapped out the suspect region to his or her satisfaction.

Figure 5:
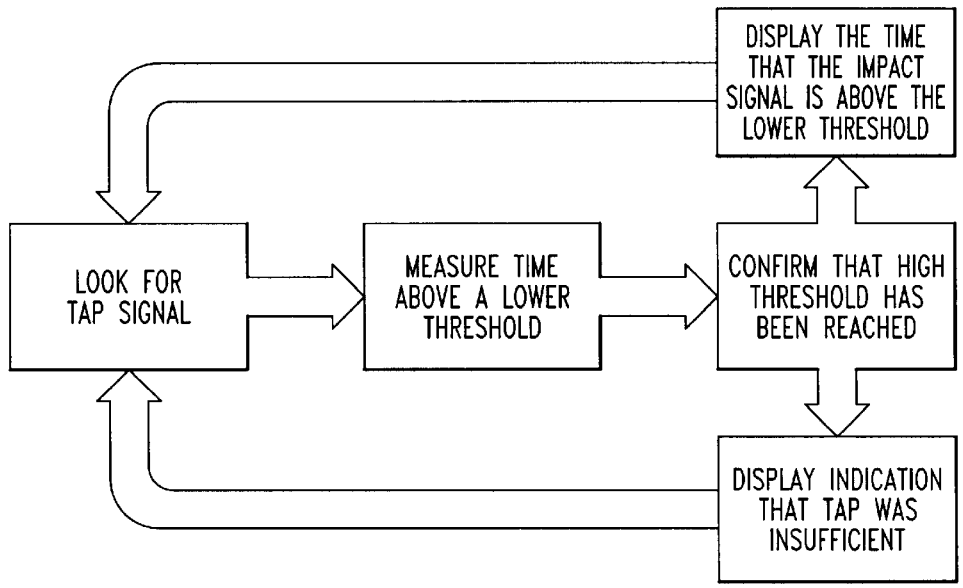
FIG. 5 is a flow chart of the measuring method used by the damage detection device.

FIG. 5 shows a diagram of the method by which the damage detection circuit produces and displays a value corresponding to the impact duration. The circuit looks for a tap signal. Once a tap signal is obtained that reaches the lower threshold level, the duration of the signal above that threshold is measured. The circuit then determines whether the high threshold had been reached at any time. If the high threshold had been reached, the circuit would display the duration of the signal above the threshold that was measured, and wait for the next tap. If the high threshold is not reached, the circuit will produce a signal indicating an improper tap. This signal could be, for instance, a light emitting diode or a display showing the value "zero." Other methods of producing such a signal are known.

Figure 6A:
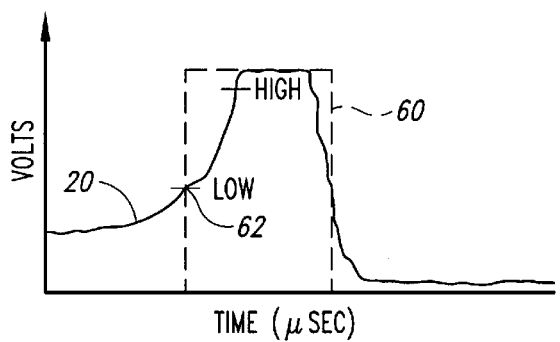
FIG. 6A is a representation of the oscilloscope signal showing an impact signal waveform for a good region with the first comparator output superimposed.
Figure 6B:
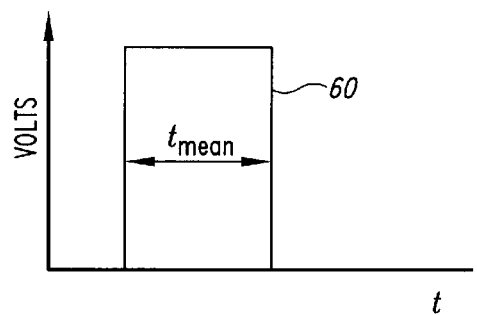
FIG. 6B represents the output from the first comparator for a good region.

FIG. 6A shows the impact signal 20 with the comparator signal 60 superimposed. The waveform is clipped, which does not adversely affect the values obtained since the duration of the signal is measured rather than the amplitude. The dashed line shows the output from the comparator, which is also shown in FIG. 6B. The output jumps from a low level to a high level once the signal reaches or exceeds the lower threshold level 62. That high level is maintained until the signal reaches or falls below the lower threshold level. The time from the start to the end of the high comparator level is the value that the rapid damage detection device is measuring. This value is being measured in microseconds although the scale will depend on the application and can be chosen to be any appropriate value.

Figure 9:
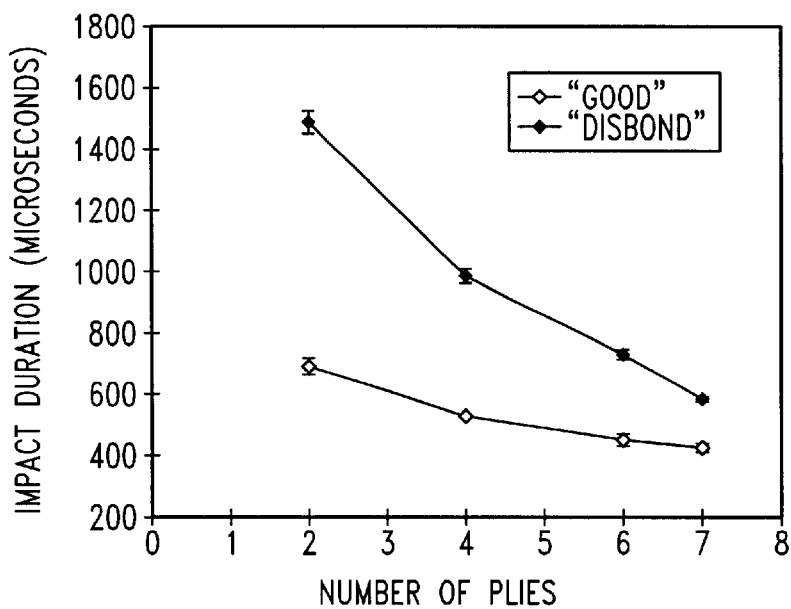
FIG. 9 shows a comparison of readings for good regions and bad regions as a function of the number of plies.

FIGS. 7A and 7B show the waveform from a tap of a bad region. The output from the first comparator, shown as dotted line 70, is much longer in duration. The relative values of the good tap and the bad tap are shown in FIG. 9 as a function of the number of plies.

Figure 8A:
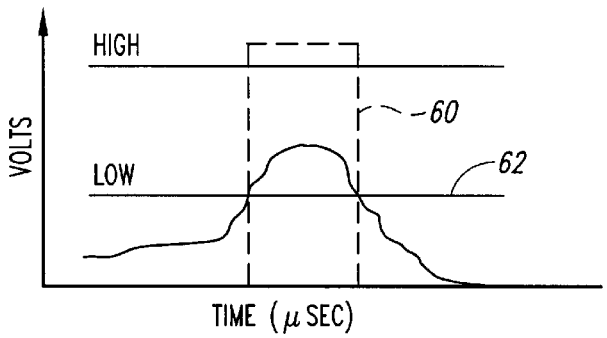
FIG. 8A is a representation of the oscilloscope signal showing an impact signal waveform for an insufficient tap with the first comparator output superimposed.
Figure 8B:
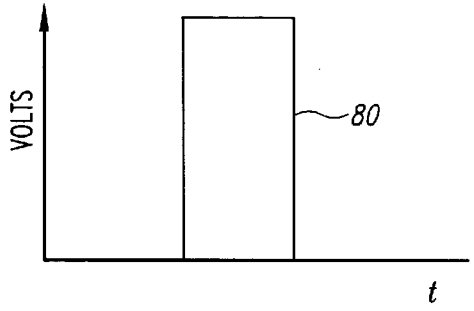
FIG. 8B represents the output from the first comparator for an insufficient tap.

FIG. 8A shows the waveform of a tap of inadequate force or energy. The first comparator output 80 is shown in FIG. 8B. The time that is measured by the circuit for this tap will never be displayed since the signal never reaches the high threshold. The circuit will instead cause an insufficient tap signal to be displayed.

It is possible to set the lower threshold and the upper threshold to any desired value. If consistent tapping is desired, the two values can be set closer together and the insufficient tap indicator can be used to train the inspector to tap more consistently. Current data suggests that consistent tapping is insignificant.

Figure 10:
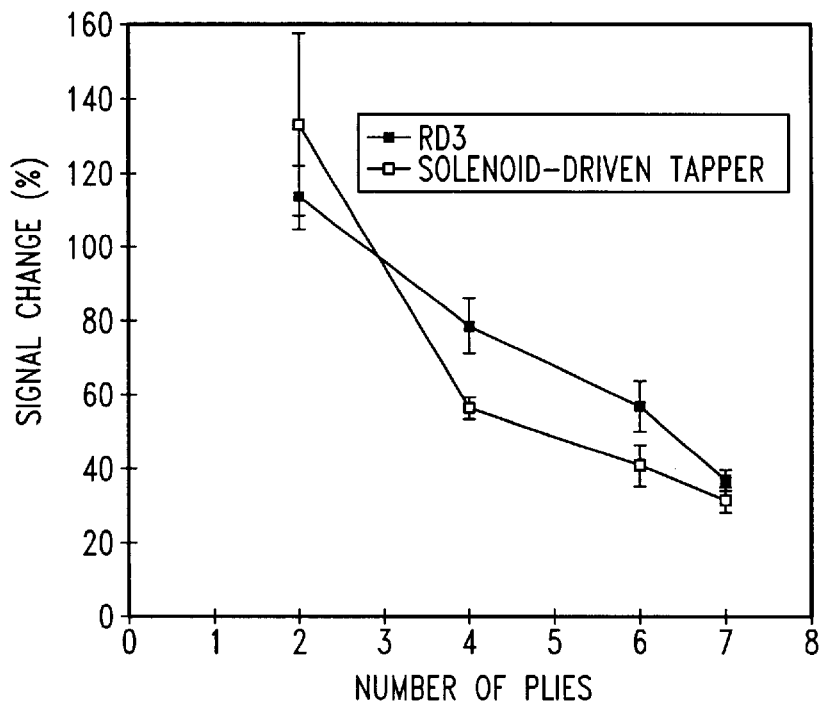
FIG. 10 shows a comparison between the damage detection device and a solenoid-driven tapper.

FIG. 10 shows a comparison of our damage detection device and a solenoid-driven tapper. The relative change between the a good region and a bad region is shown. Our device has greater sensitivity at the higher number of plies.

Figure 11:
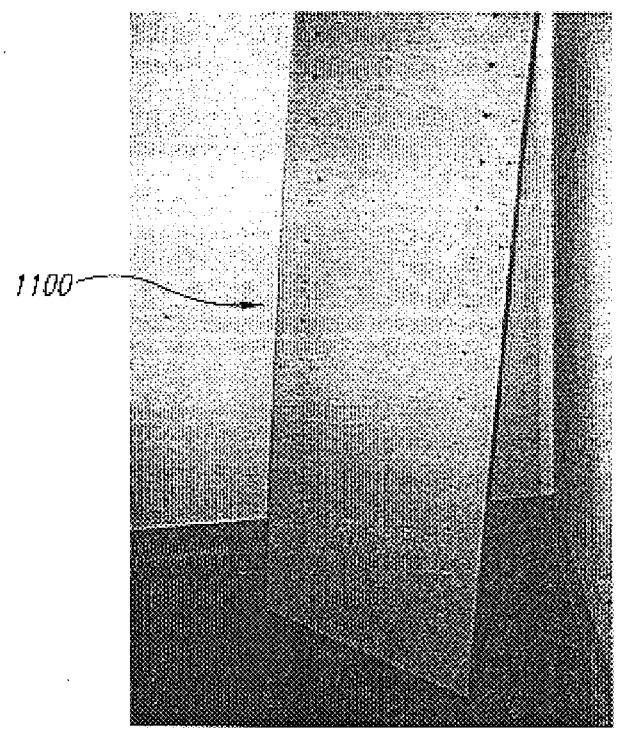
FIG. 11 shows a damaged Krueger flap.

FIG. 11 shows a damaged Krueger flap 1100. The extent of the defects is not discernible with the naked eye.

Figure 12:
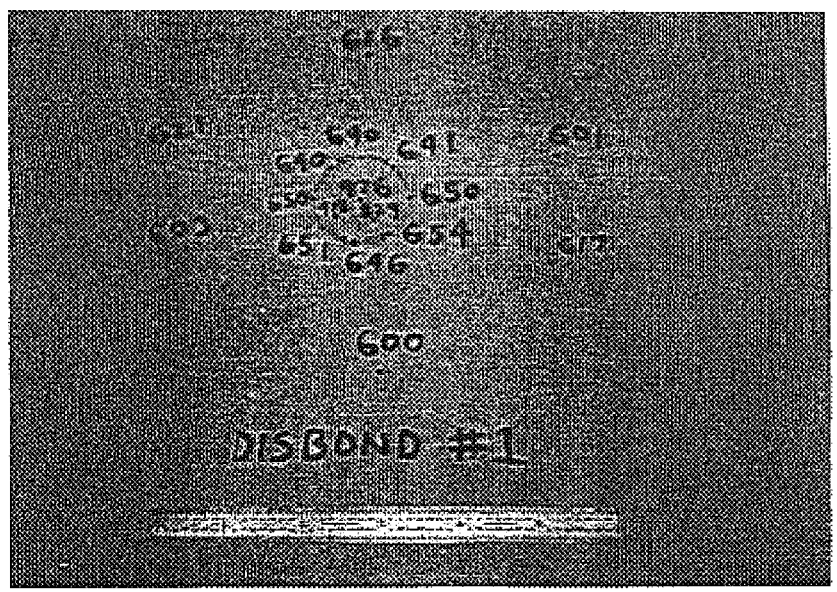
FIG. 12 shows a typical part with inspection marks indicating the extent of a damaged area.

FIG. 12 shows a typical part with inspection marks indicating the extent of the damaged area. The numbers in the 600s indicate the good region of the part and the numbers above 800 indicate a damaged region.

Figure 13:
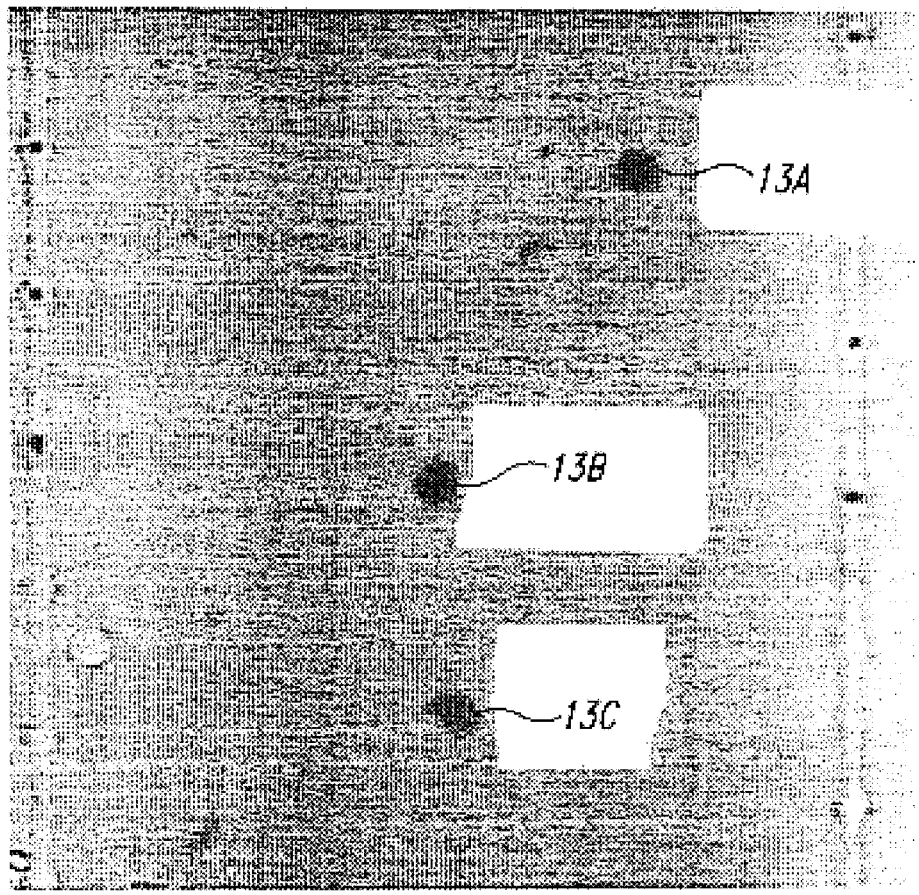
FIG. 13 shows a through transmission ultrasound (TTU) scan of a portion of the Krueger flap of FIG. 11, with the three disbonds used to test the damage detection device indicated at 13A, 13B, and 13C.

FIG. 13 shows a TTU (through transmission ultrasound) C-scan of a portion of the Krueger flap 1100. The three disbonds that were used to test our damage detection device are indicated at 13A, 13B and 13C.

Our damage detection device provides a low cost inspection device that can be used with little training and yields quantitative results. The device can test thicker laminates without being reconfigured by simply increasing the impact force. The solenoid-driven tapper does not provide this freedom as it produces consistent tap impacts. By looking at the duration of the impact signal above a certain threshold it is possible to compare a good region to a bad region and confidently determine the extent of the damage. Our method will enable flightline inspectors to make fly/no-fly decisions rapidly and confidently. The simplicity of the damage detection device and the absence of expensive electronics reduces the cost of this device, which will enable a greater number of inspectors to have ready access to this inspection method. The projected cost of this device is between U.S. $500.00 and U.S. $1000.00 compared to the U.S. $6,000 to U.S. $12,000 price for the solenoid-driven tapper currently available. The price of one device should be even lower for the coin embodiment While we have described preferred embodiments, those skilled in the art will readily recognize alternatives, variations, and modifications which might be made without departing from the inventive concept. Therefore, interpret the claims liberally with the support of the full range of equivalents known to those of ordinary skill based upon this description. The examples illustrate the invention and not intended to limit it. Accordingly, limit the claims only as necessary in view of the pertinent prior art.

We claim:

1. An apparatus for detecting defects in composite structures, comprising:
   (a) a head for striking a suspect area on the composite structure,
   (b) an accelerometer sensor mounted inside the head for detecting impact of the head against the composite structure and producing an impact signal,
   (c) a circuit connected to the sensor for converting the impact signal into a representative alphanumeric readout value by determining whether the impact was adequate to reliably measure characteristics of the impact signal representing the integrity of the composite, the circuit including a threshold comparator to make such determination, and, if the impact was adequate by rising above a predetermined threshold value, measuring with a clock the length of time that the impact was above the threshold value, the clock producing the readout value in the form of the measured, elapsed time or an equivalent value; and
   (d) an alphanumeric readout for displaying the readout value.

2. A method of determining an impact width from a test tap, comprising:
   (a) receiving an impact signal from an acceleration sensor;
   (b) passing the signal to a timing circuit in the event that the impact signal reaches in amplitude a timing threshold;
   (c) starting a clock upon passing the signal to the timing circuit and timing the duration of the amplitude of the impact signal above the timing threshold;
   (d) stopping the clock once the impact signal falls in amplitude below the timing threshold;
   (e) detecting with circuitry associated with the accelerometer whether the impact signal reached a predetermined, high amplitude threshold above the timing threshold to determine that the impact signal was created by an impact adequate for making reliable measurements of the integrity of the composite;
   (f) displaying an "insufficient impact" signal on an alphanumeric display associated with the accelerometer, if the high amplitude threshold has not been reached; and
   (g) displaying as a number on the display representative of the time measured by the timing circuit, if the high amplitude threshold has been reached.

3. A method of detecting defects in composite structures, comprising the steps of:
   (a) manually striking a hand-held tool including an accelerometer against a composite structure to produce an impact;
   (b) determining whether the impact was adequate to allow a reliable measurement of integrity of the composite structure by determining with a comparator connected to the accelerometer whether the impact produces a signal in the accelerometer that has an amplitude above a predetermined threshold;
   (c) if the impact was above the threshold, then measuring the length of time in seconds that the signal remains above a measurement amplitude threshold by triggering a clock upon the rise and fall of the test signal;
   (d) displaying the time as a value on an alphanumeric readout; and
   (e) reading the time value displayed on an alphanumeric output display.

4. A method of detecting defects in composite structure, comprising the steps of:
   (a) manually striking an accelerometer by hand against a composite structure to produce an output signal;
   (b) amplifying the output signal;
   (c) determining whether the output signal exceeds a timing threshold value;
   (d) if the output signal exceeds the timing threshold value, then measuring and recording a time during which the output signal exceeds the timing threshold value with a clock; and
   (e) then, displaying the numerical value of the time measured by the clock on an alphanumeric display of the tool.

5. A method for detecting defects in a composite structure, comprising the steps of:
   (a) manually striking a hammer by hand against a composite structure to define an impact signal in seconds from a tap at a first location which is known to be good, the hammer having an accelerometer attached to a display and a memory;
   (b) recording a good numerical value for the tap in the memory, the good value being the length of time that the amplitude of the impact signal exceeds a predetermined timing threshold as measured by a clock associated with the accelerometer;
   (c) manually striking the hammer a second time by hand against the composite structure defining a test signal for a test tap at a suspect location on the composite structure;
   (d) recording a second numerical value in seconds in the memory being the length of time that the amplitude of the test signal of the test tap is over the timing threshold;
   (e) comparing in a comparator associated with the memory the second numerical value with the good numerical value to determine whether the second value is within an acceptable range; and
   (f) generating a signal based upon the comparison indicative of whether the value is in the acceptable range.

* * * * *